(12) United States Patent
Dhuper et al.

(10) Patent No.: US 7,926,484 B2
(45) Date of Patent: *Apr. 19, 2011

(54) INTERFACE ACCESSORY FOR USE WITH AN AEROSOL INHALATION SYSTEM

(75) Inventors: Sunil Kumar Dhuper, Old Westbury, NY (US); Herbert Fred D'Alo, Madison, CT (US)

(73) Assignee: Aeon Research and Technology, Inc., Hewlett, NY (US)

( * ) Notice: Subject to any disclaimer, the term of this patent is extended or adjusted under 35 U.S.C. 154(b) by 556 days.

This patent is subject to a terminal disclaimer.

(21) Appl. No.: 11/869,492

(22) Filed: Oct. 9, 2007

(65) Prior Publication Data

US 2008/0087280 A1  Apr. 17, 2008

Related U.S. Application Data

(63) Continuation-in-part of application No. 11/632,221, filed on Jan. 15, 2007, now Pat. No. 7,841,342, which is a continuation-in-part of application No. 11/414,737, filed on Apr. 27, 2006, now Pat. No. 7,841,341, which is a continuation-in-part of application No. 11/121,688, filed on May 3, 2005, now Pat. No. 7,445,006.

(51) Int. Cl.
*A61M 16/00* (2006.01)
*A61M 15/00* (2006.01)

(52) U.S. Cl. .......... 128/203.15; 128/200.24; 128/203.12

(58) Field of Classification Search ............. 128/200.24, 128/203.12, 203.25, 204.18, 205.25, 206.12, 128/206.21; 285/24, 133.11, 382
See application file for complete search history.

(56) References Cited

U.S. PATENT DOCUMENTS

| | | | |
|---|---|---|---|
| 3,057,347 A | | 10/1962 | McGee |
| 3,903,884 A | * | 9/1975 | Huston et al. ............ 128/200.18 |
| 4,210,155 A | | 7/1980 | Grimes |
| 4,463,755 A | | 8/1984 | Suzuki |
| 4,470,412 A | | 9/1984 | Nowacki et al. |
| 4,637,528 A | | 1/1987 | Wachinski et al. |
| 4,641,644 A | | 2/1987 | Andersson et al. |
| 4,648,628 A | * | 3/1987 | Meadows et al. ............... 285/24 |
| 4,649,912 A | | 3/1987 | Collins |
| 4,823,784 A | | 4/1989 | Bordoni et al. |
| D308,576 S | * | 6/1990 | Iversen ........................ D24/129 |
| 4,951,661 A | * | 8/1990 | Sladek ..................... 128/202.27 |
| 4,953,545 A | | 9/1990 | McCarty |
| 5,012,803 A | | 5/1991 | Foley et al. |
| 5,020,530 A | | 6/1991 | Miller |
| 5,039,134 A | * | 8/1991 | Meadows et al. ............... 285/24 |
| 5,263,485 A | | 11/1993 | Hickey |
| 5,277,175 A | * | 1/1994 | Riggs et al. .............. 128/200.21 |

(Continued)

*Primary Examiner* — Steven O Douglas
*Assistant Examiner* — Annette F Dixon
(74) *Attorney, Agent, or Firm* — Leason Ellis LLP (57) ABSTRACT

An aerosol inhalation system includes a single source of gas; a connector and an accessory having a main conduit body. A nebulizer is sealingly and removably coupled to the main conduit body. A supplemental gas inlet port is in fluid communication with the connector for introducing a flow of supplemental gas from the single gas source to the patient under select conditions. The gas from the gas source that flows to the supplemental gas inlet port passes through a flow metering member that is remote from the supplemental gas inlet port that controls the flow rate of the supplemental gas to the patient interface. The flow rate of the gas through the supplemental gas inlet port is different than a gas flow rate into the nebulizer for generating the aerosolized medication.

13 Claims, 5 Drawing Sheets

U.S. PATENT DOCUMENTS

| | | | |
|---|---|---|---|
| 5,287,849 A | 2/1994 | Piper et al. | |
| 5,349,946 A | 9/1994 | McComb | |
| 5,385,140 A | 1/1995 | Smith | |
| 5,388,571 A | 2/1995 | Roberts et al. | |
| 5,479,920 A * | 1/1996 | Piper et al. | 128/204.23 |
| 5,482,031 A | 1/1996 | Lambert | |
| 5,546,930 A * | 8/1996 | Wikefeldt | 128/201.13 |
| 5,586,551 A * | 12/1996 | Hilliard | 128/203.29 |
| 5,613,489 A * | 3/1997 | Miller et al. | 128/203.28 |
| 5,617,844 A | 4/1997 | King | |
| 5,640,951 A | 6/1997 | Huddart et al. | |
| 5,727,542 A | 3/1998 | King | |
| 5,738,087 A | 4/1998 | King | |
| 5,752,502 A | 5/1998 | King | |
| 5,791,340 A | 8/1998 | Schleufe et al. | |
| 5,813,423 A | 9/1998 | Kirchgeorg | |
| 5,848,587 A | 12/1998 | King | |
| 5,865,172 A | 2/1999 | Butler et al. | |
| 6,041,777 A | 3/2000 | Faithfull et al. | |
| 6,078,730 A | 6/2000 | Huddart et al. | |
| 6,116,233 A | 9/2000 | Denyer et al. | |
| 6,192,884 B1 | 2/2001 | Vann et al. | |
| 6,340,023 B2 * | 1/2002 | Elkins | 128/200.21 |
| 6,363,932 B1 | 4/2002 | Forchione et al. | |
| 6,390,090 B1 | 5/2002 | Piper | |
| 6,427,685 B1 | 8/2002 | Ray | |
| 6,450,163 B1 | 9/2002 | Blacker et al. | |
| 6,494,202 B2 | 12/2002 | Farmer | |
| 6,550,476 B1 | 4/2003 | Ryder | |
| 6,622,725 B1 | 9/2003 | Fisher et al. | |
| 6,679,252 B2 | 1/2004 | Sladek | |
| 6,748,945 B2 | 6/2004 | Grychowski et al. | |
| 6,772,754 B1 * | 8/2004 | Mendenhall | 128/200.14 |
| 6,776,160 B2 | 8/2004 | Wang | |
| 6,799,423 B2 | 10/2004 | Piekarski | |
| 6,929,003 B2 | 8/2005 | Blacker et al. | |
| 6,976,488 B2 | 12/2005 | Halperin | |
| 6,994,083 B2 | 2/2006 | Foley et al. | |
| 7,036,500 B2 | 5/2006 | Niles et al. | |
| 7,080,643 B2 | 7/2006 | Grychowski et al. | |
| 7,131,439 B2 | 11/2006 | Blacker et al. | |
| 7,191,776 B2 | 3/2007 | Niles et al. | |
| 7,204,245 B2 | 4/2007 | Johnson et al. | |
| 7,290,541 B2 | 11/2007 | Ivri et al. | |
| 7,445,006 B2 * | 11/2008 | Dhuper et al. | 128/203.12 |
| 7,493,898 B2 | 2/2009 | King | |
| 2002/0017302 A1 | 2/2002 | Fukunaga et al. | |
| 2002/0121275 A1 | 9/2002 | Johnson et al. | |
| 2002/0129814 A1 | 9/2002 | Sladek | |
| 2003/0010336 A1 | 1/2003 | Vito | |
| 2003/0209246 A1 | 11/2003 | Schroeder et al. | |
| 2004/0011364 A1 | 1/2004 | Dhuper et al. | |
| 2004/0024372 A1 | 2/2004 | Grogan | |
| 2004/0084048 A1 * | 5/2004 | Stenzler et al. | 128/206.12 |
| 2004/0123974 A1 | 7/2004 | Marler et al. | |
| 2004/0226563 A1 | 11/2004 | Xu et al. | |
| 2004/0234610 A1 * | 11/2004 | Hall et al. | 424/489 |
| 2005/0028811 A1 | 2/2005 | Nelson et al. | |
| 2005/0092325 A1 | 5/2005 | Dionne | |
| 2005/0247313 A1 * | 11/2005 | Niles et al. | 128/203.16 |
| 2006/0231090 A1 | 10/2006 | King | |
| 2006/0231091 A1 * | 10/2006 | Camarillo | 128/200.21 |
| 2006/0260607 A1 * | 11/2006 | Dhuper et al. | 128/200.21 |
| 2007/0062531 A1 | 3/2007 | Fisher | |
| 2007/0137644 A1 * | 6/2007 | Dhuper et al. | 128/203.12 |
| 2008/0087280 A1 * | 4/2008 | Dhuper et al. | 128/200.23 |

* cited by examiner

INTERFACE ACCESSORY FOR USE WITH AN AEROSOL INHALATION SYSTEM

CROSS-REFERENCE TO RELATED APPLICATION

The present application is a continuation-in-part of U.S. patent application Ser. No. 11/632,221, filed Jan. 15, 2007 now U.S. Pat. No. 7,841,342 which is a continuation-in-part of U.S. patent application Ser. No. 11/414,737, filed Apr. 27, 2006 now U.S. Pat. No. 7,841,341 which is a continuation-in-part of U.S. patent application Ser. No. 11/121,688, filed May 3, 2005, (now U.S. Pat. No. 7,445,006, issued on Nov. 4, 2008), each of which is hereby incorporated by reference in their entirety.

1. Technical Field

The present invention relates to inhalation equipment and more particularly, relates to aerosol inhalation systems including an interface (accessory) for use in the system between a conventional part of the inhalation equipment, such as a generator, and the patient to provide in a number of applications a completely closed system that ensures that the medication delivered to the patient has a fixed concentration over time.

2. Background

Aerosol inhalation equipment is commonly used as a means to deliver medication in an aerosolized form to a patient. Aerosolized medication is typically used to treat patients with respiratory conditions, such as asthma or chronic obstructive pulmonary disease (COPD). For example, inhalation equipment is a common means for delivering medication to counter certain aliments of a patient population, including reactive airway disease, asthma, cystic fibrosis, etc.

It is generally accepted that effective administration of medication as aerosol depends on the delivery system and its position in relation to the patient. Aerosol particle deposition is influenced by particle size, ventilatory pattern, and airway architecture and effective medication response is also influenced by the dose of the medication used.

An aerosol delivery system includes three principal elements, namely a generator, a power source, and an interface. Generators include small volume nebulizers (SVN), large volume nebulizers (LVN), metered dose inhalers (MDI), and dry powder inhalers (DPI). The power source is the mechanism by which the generator operates or is actuated and includes compressed gas for SVN and LVN and self-contained propellants for MDI. The interface is the conduit between the generator and the patient and includes spacer devices/accessory devices with mouthpieces or face masks. Depending on the patient's age (ability) and coordination, various interfaces are used in conjunction with SVN and MDI in order to optimize drug delivery.

A SVN is a jet nebulizer that is powered by a compressed gas source. The medication is displaced up a capillary tube from the nebulizer's reservoir and is dispersed continuously as aerosolized particles. The aerosolized particles are spontaneously inhaled by the patient or delivered in conjunction with positive-pressure breaths. Typically, for patients greater than 3 years who are spontaneously breathing without an artificial airway and are able to cooperate, a mouthpiece with an extension reservoir should be used. For patients unable to negotiate a mouthpiece, typically children under 3 years, a face mask should be used.

An MDI is essentially a pressurized canister that contains a medication and propellant. Actuation of the MDI results in the ejection of one dose of medication as aerosolized particles, which can be spontaneously inhaled by the patient or delivered in conjunction with positive-pressure breaths. A spacer device/accessory device should be used with an MDI. A spacer device enhances delivery by decreasing the velocity of the particles and reducing the number of large particles. A spacer device with a one-way valve, i.e., holding chamber, eliminates the need for the patient to coordinate actuation and inhalation and optimizes drug delivery. A spacer device without valves requires coordination between inhalation and actuation. The MDI with spacer device and face mask is appropriate for patients, typically less than 3 years, unable to use a mouthpiece.

A DPI is a breath-actuated device that uses a gelatin capsule containing a single dose of medication and a carrier substance to aid in the dispersion of the drug. The capsule is inserted into the device and punctured. The patient's inspiratory flow disperses the dry particles and draws them into the lower airways. In spontaneously breathing patients, this device is appropriate in patients who are able to achieve a certain inspiratory flow, such as equal to or greater than 50 L/min. This will typically correspond to children about 6 years or greater.

A LVN can be used to deliver a dose of medication continuously over a period of time. A LVN is powered by a compressed gas source, and a face mask is typically used as the interface.

The two primary means for delivering aerosolized medication to treat a medical condition is an MDI or a nebulizer. MDI medication (drug) canisters are typically sold by manufacturers with a boot that includes a nozzle, an actuator, and a mouthpiece. Patients can self-administer the MDI medication using the boot alone but the majority of patients have difficulty in synchronizing the actuation of the MDI canister and patient inhalation and improve the delivery and improve the delivery of medication by decreasing oropharyngeal deposition of the aerosol drug.

Many valved chambers of this type are commercially available. Examples of such spacers include but are not limited to those structures disclosed in U.S. Pat. Nos. 4,470,412; 5,012,803; 5,385,140; 4,637,528; 4,641,644; 4,953,545; and U.S. patent application publication No. 2002/0129814. These devices are expensive and may be suitable for chronic conditions that require frequent use of MDI inhalers provided the cost and labor involved in frequent delivery of medication is acceptable to the patient. However, under acute symptoms, such devices may fail to serve the purpose and lead to an inadequate delivery of medication.

Aerosol delivery systems that use standard small volume nebulizers are commonly used in acute conditions as they are cheap and overcome the inhalation difficulties associated with actuation of MDI and synchronization of inhalation by the patient. Nebulizers are fraught with numerous problems as well. The medication dose used is about 10 times of that used with an MDI and hence the increased cost without any added proven clinical benefit. Secondly, the majority of the nebulized medication is wasted during exhalation. Thirdly, the time taken to deliver the medication is several times that of an MDI and the labor cost of respiratory therapist may outweigh the benefits of nebulizers compared with MDIs. Breath actuated nebulizers(s) with reservoir have been designed to overcome the medication waste. An example of this type of device is found in U.S. Pat. No. 5,752,502. However, these devices are expensive and still have all the other problems associated with nebulizer use alone. Other examples of aerosol inhalation devices can be found in U.S. Pat. No. 4,210, 155, in which there is a fixed volume mist accumulation chamber for use in combination with a nebulizer and a TEE connection.

Problems with prior art devices include that the devices significantly waste medication, they provide a non-uniform concentration of delivered medication, they are expensive, and they are difficult to use. Many of these devices are commercially available in which the nebulizer is directly attached to the TEE connector without any mixing chamber. All of the aforementioned devices can be used with either an MDI or a nebulizer but not both, and hence, face the difficulty associated with either system alone. Other devices have tried to overcome the above problems by incorporating a mixing chamber in the device with adaptability to be used with an MDI or standard nebulizer. U.S. patent application publication No. 2002/0121275 disclosed a device having the above characteristics. However, this device is plagued with problems that are typical to those types of devices. As with other conventional devices, the disclosed device, like the other ones, fails to incorporate some of the key features necessary for enhanced aerosol delivery.

In general, each of the prior art devices suffers from the following deficiencies: (1) the entrained airflow in the device interferes with the MDI plume as well as the plume generated by a nebulizer resulting in increased impaction losses of aerosol generated by either an MDI or nebulizer; (2) the device does not have the ability to deliver a desired precise fraction of inspired oxygen to a hypoxic patient and simultaneously deliver aerosol medication with either a metered dose inhaler (MDI) or a nebulizer; (3) the device can not deliver a gas with a desired density to improve aerosol delivery and a desired fraction of inspired oxygen to a hypoxemic patient; (4) the device does not have the ability to deliver different density gases with a desired fraction of inspired oxygen simultaneously while retaining the ability to deliver aerosol medication at the same time with either an MDI or a nebulizer; (5) the device does not have the ability to deliver a mixture of multiple gases to a patient and simultaneously maintain a desired fraction of inspired oxygen; (6) the device does not serve as a facemask for delivering varying concentrations of inspired oxygen from room air to 100% but serves solely as an aerosol delivery device; (7) the device does not have a reservoir chamber—either as a bag or as a large volume tubing to store nebulized medication that is otherwise wasted during exhalation (The holding chamber of this type of device varies from 90 cc to 140 cc and is not enough to serve as a reservoir for the volume of nebulized medication generated during exhalation is wasted); (8) there is no mechanism in the device to prevent entrainment of room air which forms the bulk of volume during inhalation (the fraction of inspired oxygen and the density of the gas mixture inhaled by the patient may vary with every breath with the device depending on the volume of entrained room air which may vary with each breath); (9) the device does not have any valve system to prevent exhaled carbon dioxide from entering the holding chamber—rebreathing of carbon dioxide from the holding chamber on subsequent inhalation can be extremely detrimental to a patient and extremely dangerous under certain clinical conditions; (10) the device does not have the capability of delivering medication with an MDI and a nebulizer simultaneously; and (11) the device has a fixed volume-holding chamber, which makes the device extremely large and cumbersome to deliver medication.

What is needed in the art and has heretofore not been available is a system that overcomes the above deficiencies and incorporates functionality to make the device a compact, user friendly, economical, and multipurpose aerosol device for both acute and chronic use with either an MDI or a nebulizer or with both devices simultaneously as warranted by the patient's clinical circumstances.

SUMMARY

An aerosol inhalation system according to one embodiment includes a single source of gas; a Y-conduit (tube) having a first leg in fluid communication with the gas source and second and third legs; and an accessory having a main conduit body and a patient interface member that delivers aerosolized medication to a mouth of the patient.

A nebulizer is sealingly and removably coupled to the main conduit body. The nebulizer includes a gas inlet port that is fluidly connected to the third leg of the Y-tube to permit gas from the single source to flow into the nebulizer to create the aerosolized medication that is delivered into the main conduit body and to the patient through the patient interface conduit. A supplemental gas inlet port is in fluid communication with the second leg for introducing a flow of supplemental gas from the single gas source to the patient interface under select conditions. The gas from the gas source that flows to the supplemental gas inlet port passes through a flow metering structure that is remote from the supplemental gas inlet port and controls the flow rate of the supplemental gas to the patient interface. The flow rate of the gas through the supplemental gas inlet port is different than a flow rate of gas into the nebulizer for generating the aerosolized medication. The flow metering structure can be part of the second leg, associated with the second leg or can be part of a connector coupled to the second leg.

Further aspects and features of the exemplary aerosol inhalation system disclosed herein can be appreciated from the appended Figures and accompanying written description.

BRIEF DESCRIPTION OF THE DRAWING FIGURES

The foregoing and other features of the present invention will be more readily apparent from the following detailed description and drawings of the illustrative embodiments of the invention wherein like reference numbers refer to similar elements and in which.

DETAILED DESCRIPTION OF PREFERRED EMBODIMENTS

Now turning to FIGS. 1 and 3-5 in which an accessory or interface element 100 according to one exemplary embodiment and for use in an aerosol delivery system is illustrated. As described below, the accessory 100 is intended for use with a nebulizer or an MDI or another piece of aerosol inhalation equipment. The accessory 100 is defined by a body 110 that can be formed of any number of different materials, including a plastic material or a metal. The accessory 100 is essentially a hollow body 110 that has a first end (inlet end) 112 and an opposing second end (outlet end) 114. The accessory 100 is intended to act as a fluid connector in that it is fluidly attached to another piece of equipment, such as a facemask, that is directly coupled to the patient's mouth, as well as being fluidly attached to an actuatable device that generates the aerosol particles (aerosolized medication) that are delivered to the patient.

In the illustrated embodiment, the body 110 has a main section 116 that includes a number of arms or feet that extend outwardly therefrom, with the inlet end 112 being formed at the end of a first leg 120 that is formed at a right angle to the main section 116. The main section 116 includes a second leg 130 that extends outwardly therefrom between the first leg 120 and the outlet end 114 and a third leg 140 that is located between the outlet end 114 and the second leg 130. The third leg 140 is located proximate the outlet end 114, while the second leg 130 is closer to the first leg 120. The first, second and third legs 120, 130, 140 are thus tubular structures that are in fluid communication with the interior of the tubular main section 116 and are open at their opposite distal ends to receive an object (such as a conduit or connector) or a fluid, etc.

The main section 116 includes a fourth leg 150 that extends outwardly from the main section 116 and is in fluid communication with the interior of the main section 116. Like the other legs, the fourth leg 150 is a tubular structure that is open at its distal end for an attachment to an object (conduit). In the illustrated embodiment, the first, second and third legs 120, 130, 140 extend outwardly from an underside of the tubular main section 116, while the fourth leg 150 extends outwardly from the opposite top side of the tubular main section 116. The fourth leg 150 is located between the second and third legs 130, 140.

The main section 116 is the part of the accessory 100 that is intended to be connected to equipment that is placed over the patient's nose and mouth. Thus, the main section 116 (main conduit) is the principal pathway for fluid, such as air and the aerosol particles, to either enter the patient in the case of aerosol particles and air or to be discharged from the patient as in the case of exhaled gases, such as carbon dioxide.

The first leg 120 serves as a port or connector for mating with a device 200 that generates a gas flow that is intended to be breathed in by the patient. For example, the device 200 can be in the form of a nebulizer or even an MDI or the like. In the illustrated embodiment, the device is in the form of a nebulizer 200 that is fluidly connected to a gas source via a nebulizer conduit 215. The nebulizer 200 is fluidly and sealingly connected to the first leg 120 so that the gas and aerosolized particles generated by the nebulizer 200 are delivered into the interior of the main section 116 of the accessory 100. Any number of techniques can be used to couple the nebulizer 200 to the first leg 120, such as threadingly, snap-fittingly, frictionally, etc., the two together.

In one embodiment, the accessory 100 is intended for use with a nebulizer, generally indicated at 200, and therefore includes a holding chamber 300 into which the aerosol particles can be stored prior to the patient inhaling. The holding chamber 300 is preferably formed as a member that is collapsible and expandable depending upon whether gas is being delivered thereto or being evacuated therefrom. The holding chamber 300 thus can have a number of different structures that have a variable dimension, such as a variable length or a variable width. In one embodiment, the holding chamber 300 is defined by a bellows-type structure that can either expand or collapse/constrict depending upon the force applied. As with other accessories of this type, the holding chamber 300 is intended to receive and store the aerosol particles prior to the patient inhaling them by means of the accessory 100 and the facemask.

In the illustrated embodiment, the holding chamber 300 is in the form of an expandable/collapsible bag (reservoir bag) or similar type structure. According to one aspect of the present invention, the holding chamber 300 is in the form of a bi-furcated bag or the like 310 as shown in FIG. 1. More specifically, the bag 310 is bi-furcated and has two independent distinct compartments, namely a first compartment 320 and a second compartment 330. Since the two compartments 320, 330 are distinct from one another (no fluid communication there between), the bag 310 has a first port 340 that forms an entrance and is in fluid communication with the first compartment 320, as well as a second port 350 that forms an entrance and is in fluid communication the second compartment 330. A separating wall or membrane 360 is formed as part of the bag 310 and serves to divide the bag 310 into the first and second compartments 320, 330. The body of the bag 310, as well as the separating wall 360, is preferable formed of a flexible material, such as a fabric that permits the bag 310 to either expand as when fluid enters the bag 310 or contract (collapse) as when the fluid is evacuated from the bag 310. The first port 340 is formed on one side of the separating wall 360, while the second port 350 is formed on the other side of the separating wall 360. Both the first and second ports 340, 350 are typically defined by a hollow stem or boss.

The first port 340 includes a complementary fastening feature that permits it to be sealingly attached to the third leg 140 of the accessory 100, and similarly, the second port 350 includes a complementary fastening feature that permits it to be sealingly attached to the second leg 130. For example, the first and second fastening features can be in the form of threads that mate with complementary threads that are part of the legs 140, 130, respectively. Other fastening means, such as locking means or mechanical fits, such as a frictional fit, can likewise be used so long as the accessory 100, and in particular, the second and third legs 130, 140, are sealingly attached to the bag 310. While, the fastening features can be in the form of threads, it will be appreciated that in many applications and embodiments, the third and second legs 140, 130 and the first and second ports 340, 350 simply mate with one another via a frictional interface fit between two complementary stems.

The first port 340 of the bag 310 also preferably includes a gas inlet port 342 that extends outwardly therefrom and is constructed to attach to a gas source 370. More specifically, the gas inlet port 342 is in fluid communication with and provides an entrance into the first port 340 and is in the form of a tubular structure that has a distal end 344. The end 344 is meant to be attached to the gas source 370 by any number of techniques, including using a gas conduit, such as tubing or the like, that extends from the gas source 370 to the gas inlet port 342. The gas source 370 is preferably connected to a control system or regulator or the like that permits the flow rate of the gas source 370 to be carefully controlled and varied by means, such as valve assemblies and the like that are associated therewith (e.g., valve assembly within the gas conduit).

The gas source 370 can hold any number of different types of gases that are intended for inhalation by the patient through the accessory 100.

The accessory 100 includes a number of different valve assemblies that are positioned within the body 110. More specifically, a first valve assembly 400 is disposed within the open second end 114 of the main section 116 and in the illustrated embodiment, the first valve assembly 400 functions as an exhalation valve. The first valve assembly 400 includes a valve element 402 which is positionable between an open position and a closed position and which can be any number of different types of valve structures so long as they function in the intended manner and provide the desired results. The valve 402 typically seats against a valve seat 404 that is formed at the second end 114 when the valve 402 is closed. The illustrated valve 402 is a one-way flap valve that presses against the valve seat 404 on inhalation and completely occludes the open second end 114 to prevent any room air entrainment (i.e., not allowing the air from the atmosphere to enter into the main section 116 on inhalation). On exhalation, the flap valve 402 moves away from the flap valve seat 404 for the air exhaled by the patient to escape into the atmosphere from the main section 116 by flowing through the fourth leg 150 from a mask or the like and then through the main section 116 and through the opening formed at the second end 104. The open second end 104 is the only means for the exhaled air to escape as will be appreciated below since the four legs 120, 130, 140, 150 are connected to devices, are capped or otherwise not open.

A second valve assembly 410 is provided and functions as an inhalation valve in that the valve moves between an open position and a closed position depending upon whether the patient is inhaling or exhaling. The second valve assembly 410 is disposed within the body 110 and in particular, the second valve assembly 410 is disposed within the main section 116 at a location between the second leg 130 and the fourth leg 150 such that when the second valve assembly 410 is in an open position, fluid can flow from both the first leg 110 and the nebulizer 200, as well as from the second leg 130 and the second compartment 330 of the bag 310, and into the fourth leg 150 where it can flow into the patient's mask and into the patient's respiratory system.

The second valve assembly 410 includes a valve element 412 that can be any number of different types of valve structures so long as they function in the intended manner and provide the desired results. As shown in FIG. 5, the valve 412 typically seats against a valve seat 414 that is formed within the main section 116 when the valve 412 is closed. The illustrated valve 412 is a one-way flap valve that presses against the valve seat 414 on exhalation and completely occludes the main section 116 to prevent any exhaled air to flow from the mask and fourth leg 150 and into either the second compartment 330 of the bag 310 or the first leg 120. On inhalation, the flap valve 412 moves away from the flap valve seat 414 to permit the gas from the nebulizer 200 and/or gas stored in the second compartment 330 of the bag 310 to flow into and through the main section 116 and into the fourth leg 150 where it flows into the mask to the patient.

As in FIG. 4, a third valve assembly 420 is provided and is disposed in the third leg 140 or it can be provided in the stem that defines the first port 340 that is associated with the bag 310. The third valve assembly 420 functions as an inhalation valve in that the valve moves between an open position and a closed position depending upon whether the patient is inhaling or exhaling.

The third valve assembly 420 includes a valve element 422 that can be any number of different types of valve structures so long as they function in the intended manner and provide the desired results. The valve 422 typically seats against a valve seat 424 that is formed within either the third leg 140 or first port 340 when the valve 422 is closed. The illustrated valve 422 is a one-way flap valve that presses against the valve seat 424 on exhalation and completely occludes the third leg 140 or first port 340 to prevent any exhaled air to flow from the mask and fourth leg 150 and into either the first compartment 320 of the bag 310. On inhalation, the flap valve 422 moves away from the flap valve seat 424 to permit the gas from the first compartment 320 of the bag 310 to flow into and through the main section 116 and into the fourth leg 150 where it flows into the mask to the patient.

While the two compartments 320, 330 of the bag 310 are illustrated as having equal or about equal volumes, it will be appreciated that the bag 310 can be constructed so that one of the compartments 320, 330 has a greater volume. For example, the first compartment 320 that serves as the nebulizer holding compartment can have a greater volume than the second compartment 330 which receives the supplemental gas to backup the nebulized medication holding chamber.

The first leg 120 is intended to be fluidly attached to the device that generates the aerosol particles (medication) that is delivered to the patient and preferably, as illustrated, the first leg 120 is fluidly connected to the nebulizer 200. More specifically, a connector 212 of a conduit (tube) 210 of the nebulizer 200 is sealingly attached to the first leg 120 so that the nebulized medication is delivered through the conduit 210 and into the interior of the first leg 120 and when the second valve element 412 is open, the nebulized medication (aerosol particles) travels the length through the first leg 120 and a portion of the main section 516 and through the opening defined by the valve seat 414 and into the fourth leg 150 and then into the equipment (facemask) that delivers the medication to the patient. This is the sequence of events when the patient inhales. Conversely, when the patient exhales, the second valve element 412 closes; however, the nebulizer 200 continues to deliver the nebulized medication through the first leg 120 into the interior of the main section 116. Since the second valve element 412 is closed when the patient exhales prior to the next inhalation, the nebulized medication can not flow past the valve assembly 410 and into the fourth leg 150 but instead flows through the second leg 130 through the second port 350 and into the second compartment 330 of the bag 310.

The second compartment 330 of the bag 310 is therefore intended to act as a main reservoir bag in that the second compartment 330 receives and holds the nebulized medication until the patient inhales. The second compartment 330 of the bag 310 thus expands until the patient inhales at which time the second valve element 412 opens and the inhalation of the patient draws the nebulized medication out of the second compartment 330 into the main section 116 and then into the fourth leg 150 where it is delivered to the patient.

There are some circumstances where an insufficient amount of nebulized medication is present in the second compartment 330 of the bag 310. This may result because the flow rate of the nebulizer 200 is insufficient for the patient as when the patient has a greater body weight than the flow rate setting of the nebulizer 200. When this does occur, the patient experiences a very uncomfortable feeling in that the patient will experience an insufficient air flow to the lungs and therefore will begin to breathe more deeply and rapidly. In other words, the patient may begin feeling as though they need to gasp for air to breathe.

The present invention overcomes such potential deficiency in air flow to the patient by providing the first compartment 320 in the bag 310 which acts as a supplemental air source for the patient due to the first compartment 320 being attached to a supplemental gas source, generally indicated at 370. Preferably, the gas source 370 connects to the stem of the first port 340 as shown in the figures; however, it is possible for the gas source 370 to be directly connected to the first compartment 320 of the bag 310. In any event, the gas source 370 is directly and fluidly connected to the first compartment 320 and therefore, the gas is delivered into the first compartment 320. As with the flow of nebulized medication into the second compartment 330, the flow of the gas source 370 into the first compartment 320 causes the first compartment 320 to expand as the bag 310 is filled with gas.

It will be appreciated that the gas source 370 serves as a supplemental gas since gas stored in the first compartment 320 is in selective fluid communication with the main section 116 and therefore, can flow to the patient under certain circumstances as discussed below. In other words, if there is insufficient gas in the form of nebulized gas in the second compartment 330, when the patient inhales, then the patient will not experience the above described breathing problems since the first compartment 320 is open to the patient through the main section 116 and therefore, the patient can inhale the supplemental gas that is present in the first compartment 320 to make up for any shortfall in gas in the second compartment 330.

The gas source 370 typically has an associated valve assembly (not shown) that is external to the system and is typically at the gas source 370 for controlling the flow rate of the gas source 370 into the first compartment 320. The valve assembly is preferably an adjustable valve that controls the flow rate of the supplemental gas into the first compartment 320. Any number of different valve mechanisms are suitable for this type of application and typically include an adjustable part, such as a dial, that permits the physician to easily alter and change the flow characteristics. For example, the valve mechanism can include an adjustable member that when manipulated either sequentially closes or opens the opening formed in the conduit that delivers the supplemental gas to the first compartment 320.

Thus, the physician can initially set the valve at one setting which the physician believes will provide a sufficient supplemental gas flow into the first compartment 320 based on the physician's past experiences and based on certain characteristics of the patient, such as the size and weight of the patient. For example, when the patient is a large adult or even a large child, the flow rate of the nebulized medication into the second compartment 330, even when it is set at a maximum flow rate, may not be sufficient and therefore, this could result in the patient receiving a low level of air and feeling the above noted discomfort. The gas source 370 thus supplements the gas flow of the nebulizer 200 and makes up for any deficiency so that the patient breaths smoothly throughout the procedure.

When setting the valve, the physician will keep in mind that it may not be desirable to set the flow rate of the supplemental gas at too high a value since this will result in the first bag compartment 320 expanding and also, results in the supplemental gas source 370 mixing with the nebulized medication as the patient inhales, thereby causing a decrease in the inhaled concentration of the medication. As mentioned before, it is desirable to try to keep as fixed as possible the concentration of the inhaled medication. Since the first compartment 320 is fluidly connected to the main section 116 via the third leg 140 and is fluidly connected to the first valve assembly 400, any excess build up of supplemental gas in the first compartment 320 can be vented through the first valve 402 each time the patient exhales since the second valve assembly 410 closes when the patient exhales and the supplemental gas can not flow past the second valve assembly 410 toward the other legs and the second compartment 330 of the bag 310.

In the event that the initial setting of the valve is not optimal in that the too much supplemental gas is being delivered to the first bag compartment 320 or too little supplemental gas is being delivered to the first bag compartment 320, the physician simply needs to make the necessary adjustment to the valve to either immediately reduce or increase, respectively, the supplemental gas flow into the first bag compartment 320. This can be done by simply turning or otherwise manipulating the valve. It is also very easy for the physician to determine whether the flow rate of the supplemental gas source 370 is optimal since the physician can observe the bag 310 and more particularly, can observe whether either the first bag compartment 320, the second compartment 330 or both compartments 320, 330 appear to be excessively collapsed (thus indicating an increase in flow rate is needed) or excessively expanded or extended (thus indicating a decrease in flow rate is needed). The physician can simply and immediately alter the flow rate and thus, the accessory 100 is tailored to be used with a whole range of different types of patients, from small infants up to large adults.

A supplemental gas valve assembly is preferably provided for controlling the flow of the supplemental gas out of the first compartment 320 and into the third leg 140 and more particularly, to permit flow of the supplemental gas from the first bag compartment 320 into the third leg 140, through the main section 116 and ultimately to the patient when the patient inhales and conversely, preventing the flow of supplemental gas from the first bag compartment 320 into the third leg 140 when the patient exhales. It will also be appreciated that when valve assembly closes during exhalation, the exhaled air that includes waste gases is not permitted to flow into the first bag compartment 320 where it could then be drawn into the patient at the next inhalation movement of the patient.

Figure 1:
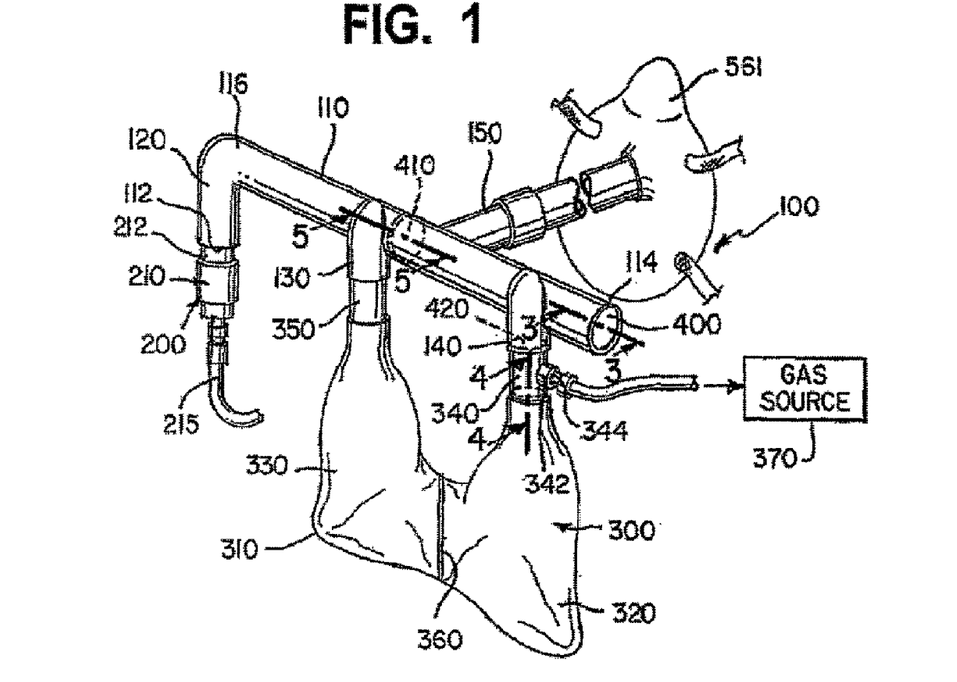
FIG. 1 is a perspective view of an accessory for use in an aerosol inhalation system according to a first embodiment.
Figure 2:
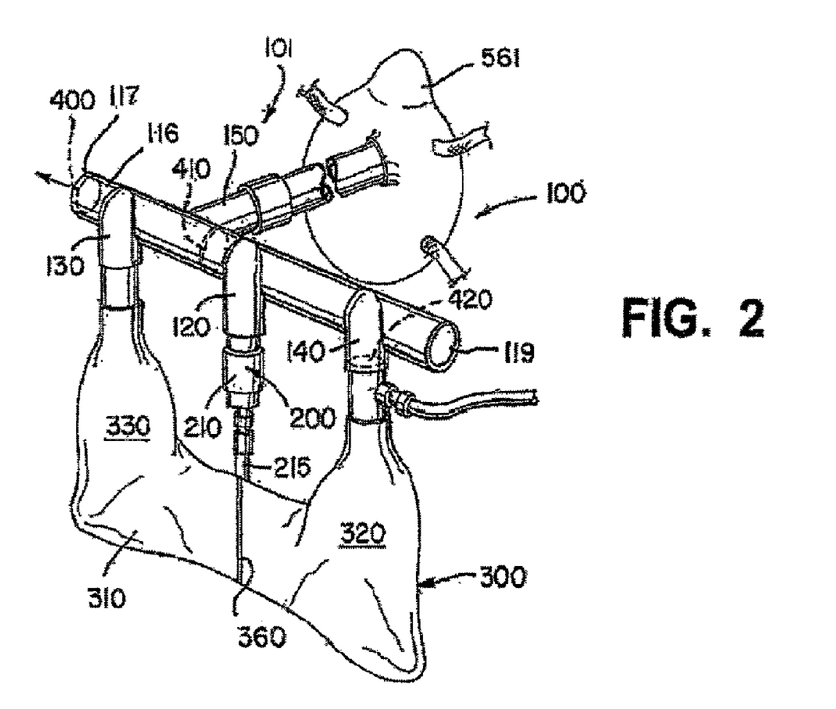
FIG. 2 is a perspective view of an accessory for use in an aerosol inhalation system according to a second embodiment.
Figure 3:
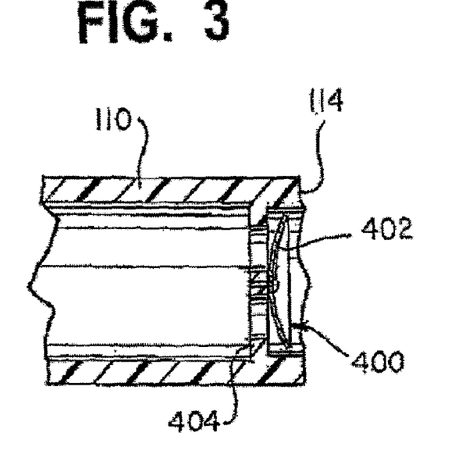
FIG. 3 is a partial cross-sectional view taken along the line 3-3 of FIG. 1.
Figure 4:
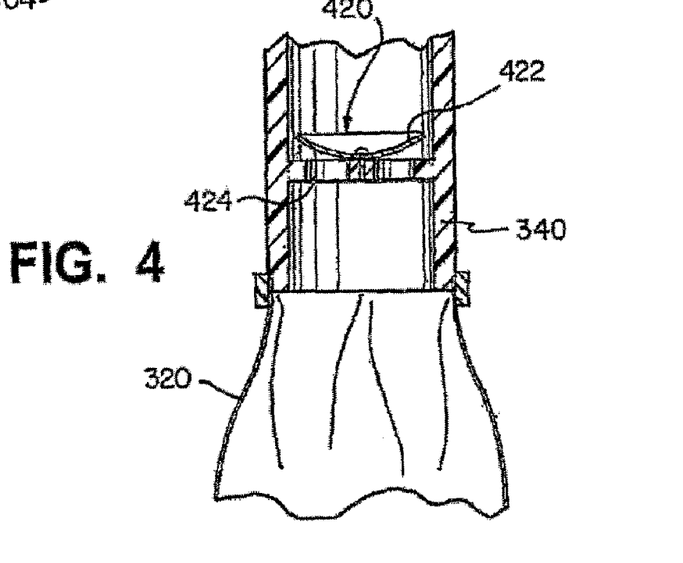
FIG. 4 is a partial cross-sectional view taken along the line 4-4 of FIG. 1.
Figure 5:
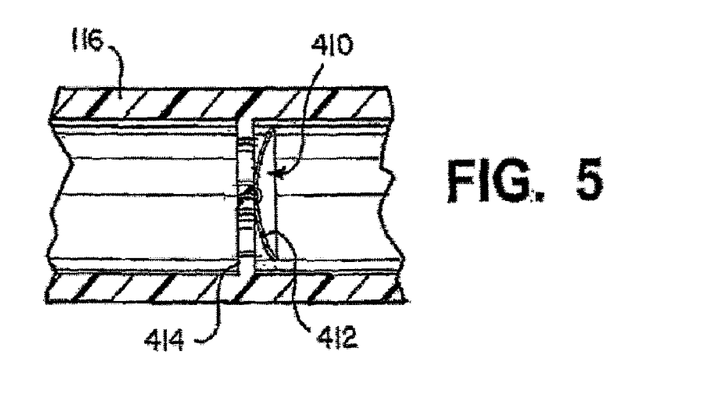
FIG. 5 is a partial cross-sectional view taken along the line 5-5 of FIG. 1.

Now referring to FIG. 2 in which another embodiment of an accessory 101 is illustrated. The accessory 101 is similar to the accessory 100 and therefore, like elements are numbered alike. In the accessory 101, the first leg 120 no longer is formed at one end of the main section 116 but rather is formed in the middle of the main section between the fourth leg 150 and the second leg 130 which is located closer to one end of the main section 116. In this design, the first leg 120 is closer to the fourth leg 150 and since the first leg 120 is still fluidly connected to the nebulizer 200, the length of the gas flow path from the nebulizer 200 to the face mask is less in this embodiment than in the embodiment of FIG. 1 due to the relative positions of the first and fourth legs 120, 150.

Since the first leg 120 is not formed at the end of the main section 116 in this embodiment, the main section 116 has an open end 117 and a closed end 119. The second leg 130 is located proximate the open end 117.

As shown, the first leg 120 is disposed between the second valve assembly 410 and the second leg 130 and in particular, the first leg 120 communicates with the interior of the main section 116 at a location that is near the second valve element 412. It will be appreciated that in this embodiment, the nebulizer 200 is located in front of/downstream from the gas flow from the second compartment 330 of the bag 310 and the present applicants have discovered that the placement of the nebulizer 200 in this location results in improved performance and improved drug delivery since the aerosolized medication is located closer to the face mask as measured along the gas flow path. In addition, this location for the nebulizer 200 permits the gas flow from the second compartment 330 of the bag 310 to assist in carrying the aerosolized medication to the fourth leg 150 and into the patient's mask or the like. In other words, the gas flow from the second compartment 330 acts to entrain the aerosolized medication that is flowing through the first leg 120 from the nebulizer 200.

The first valve 400 is located in the open end 117 of the section 116.

The operation of the components is the same in this embodiment as in the other embodiments. For example, the valve assemblies 400, 410, 420 operate the same or similar in both embodiments. The first leg 120 is positioned close to the second valve assembly 410 such that once the valve element 412 opens upon inhalation, the gas and aerosolized medication from the nebulizer 200 flows through the valve element 412 and into the fourth leg 150 to the patient.

It will also be appreciated that in each of the embodiments of FIGS. 1 and 2, the first leg 120 can be capped or otherwise sealed as when nebulizer 200 is not used with the respective accessory. In this design, the bag 310 can serve as a means for delivering a gas, such as oxygen or heliox, etc., to the patient. In particular, gas source 370 provides gas that is routed through the first compartment 320 of the bag 310 and into the main section 116 and then into the fourth leg 150 to the face mask.

Figure 6:
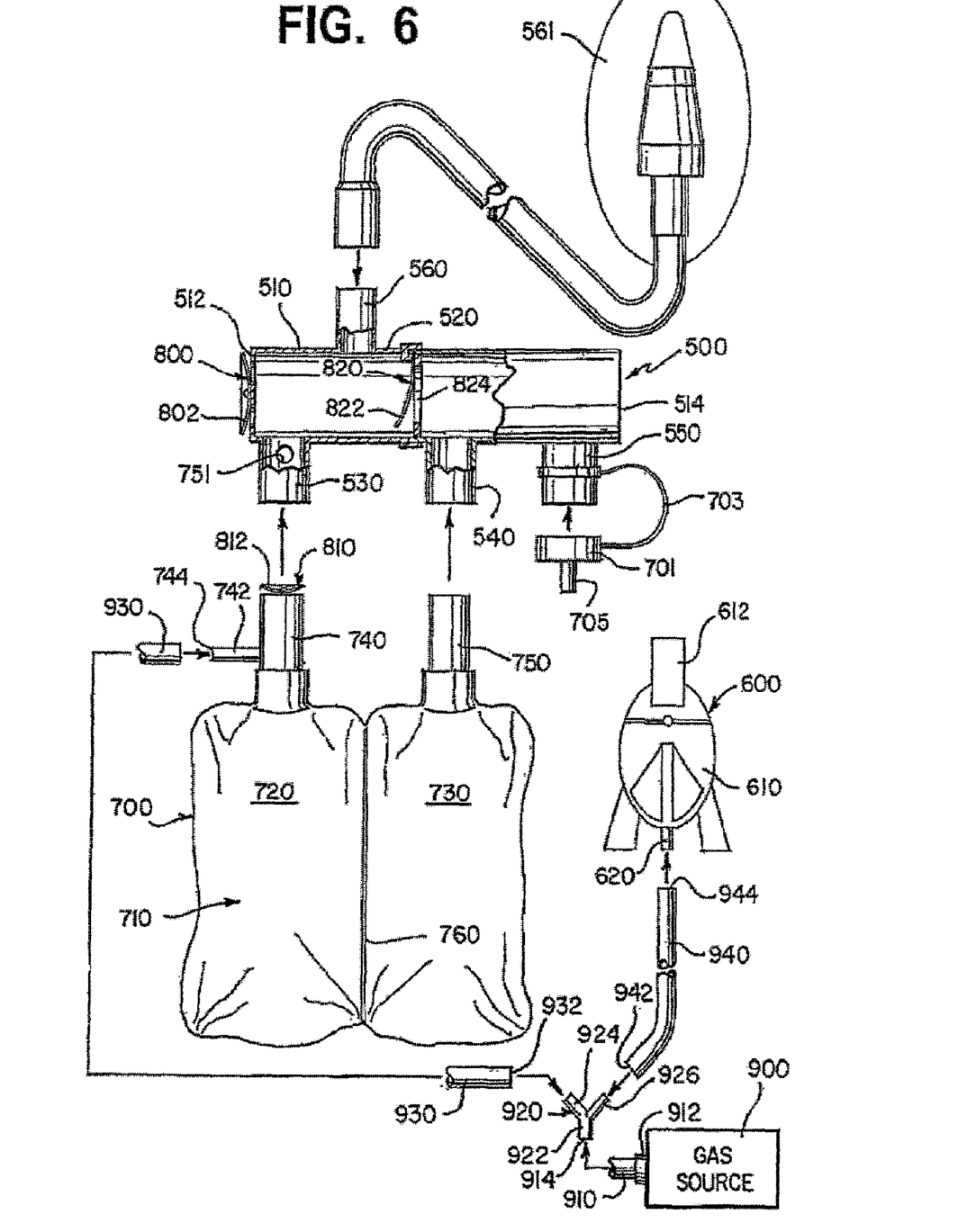
FIG. 6 is a side elevation view, in cross-section, of an accessory for use in an aerosol inhalation system according to a third embodiment with the parts thereof being exploded.
Figure 7:
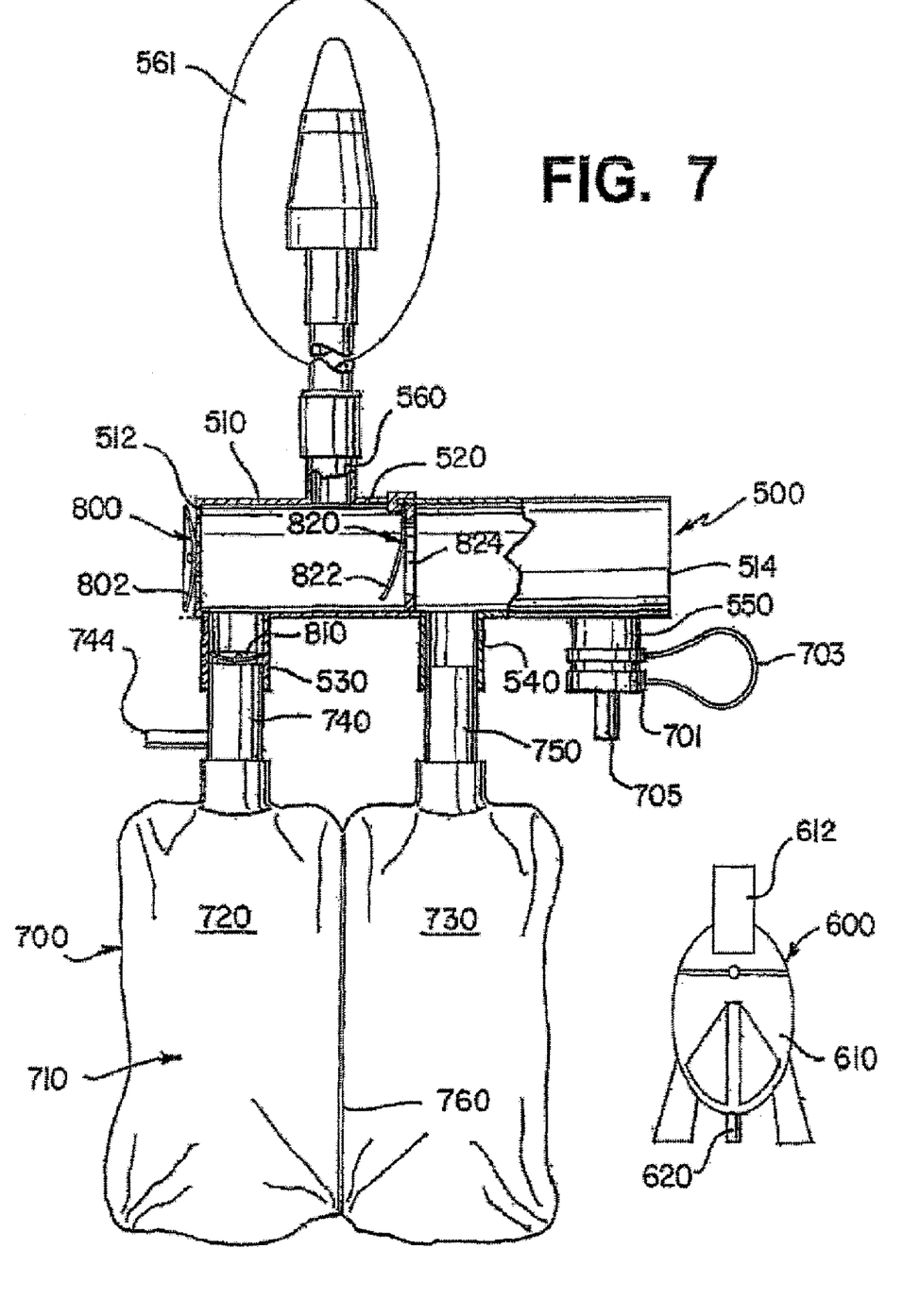
FIG. 7 is a side elevation view, in cross-section, of the accessory of FIG. 6 with the parts of the system of FIG. 6 being attached to one another.

Referring now to FIGS. 6-7 in which yet another embodiment of the present invention is illustrated. In this embodiment, an accessory 500 is illustrated and is similar in construction to the accessories 100 and 300; however, as described below, there are several key differences.

As with the other accessories, the accessory 500 is intended for use with a nebulizer or an MDI or another piece of aerosol inhalation equipment. The accessory 500 is defined by a body 510 that can be formed of a number of different materials, including plastics or even metals. The accessory 500 is essentially a hollow body 510 that has a first end 512 and an opposite closed second end 514. The accessory 500 is intended to act as a fluid connector in that it is fluidly connected to another piece of equipment, such as a facemask, that is directly coupled to the patient's mouth, as well as being fluidly attached to an actuatable device that generates the aerosol particles (aerosolized medication) that are delivered to the patient.

In the illustrated embodiment, the body 510 has a main section 520 that includes a number of arms or feet that extend outwardly therefrom. More specifically, a first leg 530 is formed at or proximate the first end 512 of the body 510, a second leg 540 is formed in an intermediate region of the body 510 and a third leg 550 is formed at or proximate the second end 514. In other words, the second leg 540 is formed between the first and third legs 530, 550. The first, second and third legs 530, 540, 550 are tubular structures that are in fluid communication with the interior of the tubular main section 520 and are open at their opposite distal ends to receive an object (such as a conduit or connector, etc.) or a fluid, etc.

The main section 520 also includes a fourth leg 560 that extends outwardly from the main section 520 and is also in fluid communication with the interior of the main section 520. Like the other legs, the fourth leg 560 is a tubular structure that is open at its distal end for attachment to an object, such as a mask or mouthpiece or the like, generally indicated at 561. In the illustrated embodiment, the first, second and third legs 530, 540, 550 extend from an underside of the main section 520, while the fourth leg 560 extends from a top side of the main section; however, this is merely an exemplary arrangement, and the relative positions of the legs can be varied, including having the legs be disposed at less than 90 degrees from one another. The fourth leg 560 is located between the first and second legs 530, 540.

The main section 520 is part of an accessory that is intended to be connected to equipment that is placed over the patient's nose and mouth. Thus, the main section 520 (main conduit) is the principal pathway for fluid to either enter the patient in the case of aerosol particles and air (or other fluid) or to be discharged from the patient as in the case of exhaled gases, such as carbon dioxide.

Unlike the embodiments shown in FIGS. 1 and 2, the accessory 500 is intended to be connected to a single gas source, as opposed to two separate gas sources. More specifically, the second end 514 is a closed end of the main section and the third leg 550 serves as a port or connector for mating with a device 600 that generates a gas flow that is intended to be breathed in by the patient. For example, the device 600 can be in the form of a nebulizer or even an MDI or the like. In the illustrated embodiment, the device 600 is shown exploded from the main section 520 and is in the form of a nebulizer body 610 that includes the medication be to be delivered and has a leg 612 that is sized and shaped to be received into the third leg 550. The leg 612 is thus a hollow tubular structure that is matingly and frictionally received and held within the third leg 550 when it is opened. FIG. 7 shows a removable cap 701 disposed within the third leg 550; however, when the nebulizer 600 is to be connected to the main section 520, the cap 701 is simply removed from the third leg 550 so as to fully open up the third leg 550. The nebulizer 600 is thus slidingly inserted into the third leg 550 and can later be removed therefrom.

In addition to having a compartment for holding the medication to be aerosolized, the nebulizer body 610 has a conduit 620 that is intended to be fluidly connected to a source of gas for creating the aerosolized medication. For example, a gas conduit (tube) can be connected to a free end of the conduit 620 for providing gas to the nebulizer 600.

The cap 701 can be attached to the third leg 550 by means of a flexible strap 703 or the like so that when the cap 701 is removed from the third leg 550, the cap 701 can simply hang from the third leg 550, thereby reducing the chances that it might be misplaced, etc. The cap 701 has a nipple 705 or the like that is a hollow conduit that includes a bore or through hole that extends completely through the cap 701, thereby permitting fluid communication between the exterior and the interior of the third leg 550, and thus, the interior of the main section 520.

As with the other embodiments, the accessory 500 is intended for use with the nebulizer 600 and therefore includes a holding chamber 700 into which the aerosol particles can be stored prior to the patient inhaling. The holding chamber 700 is preferably formed as a member that is collapsible and expandable depending upon whether gas is being delivered thereto or being evacuated therefrom. The holding chamber 700 thus can have a number of different structures that have a variable dimension, such as a variable length or a variable width. In one embodiment, the holding chamber 700 is defined by a bellows-type structure that can either expand or collapse/constrict depending upon the force applied. As with other accessories of this type, the holding chamber 700 is intended to receive and store the aerosol particles prior to the patient inhaling them by means of the accessory 500 and the facemask.

In the illustrated embodiment, the holding chamber 700 is in the form of an expandable/collapsible bag (reservoir bag) or similar type structure. According to one aspect of the present invention, the holding chamber 700 is in the form of a bi-furcated bag or the like 710 as shown in FIG. 6. More specifically, the bag 710 is bi-furcated and has two independent distinct compartments, namely a first compartment 720 and a second compartment 730. Since the two compartments 720, 730 are distinct from one another (no fluid communication there between), the bag 710 has a first connector 740 that forms an entrance and is in fluid communication with the first compartment 720, as well as a second connector 750 that forms an entrance and is in fluid communication the second compartment 730. A separating wall or membrane 760 is formed as part of the bag 710 and serves to divide the bag 710 into the first and second compartments 720, 730. The body of the bag 710, as well as the separating wall 760, is preferable formed of a flexible material, such as a fabric that permits the bag 710 to either expand as when fluid enters the bag 710 or contract (collapse) as when the fluid is evacuated from the bag 710. The first connector 740 is formed on one side of the separating wall 760, while the second connector 750 is formed on the other side of the separating wall 760. Both the first and second connector 740, 750 are typically defined by a hollow stem or boss.

The first connector 740 includes a complementary fastening feature that permits it to be sealingly attached to the first leg 530 of the accessory 500, and similarly, the second connector 750 includes a complementary fastening feature that permits it to be sealingly attached to the second leg 540. For example, the first and second fastening features can be in the form of threads that mate with complementary threads that are part of the legs 530, 540, respectively. Other fastening means, such as locking means or mechanical fits, such as a frictional fit, can likewise be used so long as the accessory 500, and in particular, the second and third legs 530, 540, are sealingly attached to the bag 710. While, the fastening features can be in the form of threads, it will be appreciated that in many applications and embodiments, the third and second legs 530, 540 and the first and second connectors 740, 750 simply mate with one another via a frictional interface fit between two complementary stems.

The first connector 740 of the bag 710 also preferably includes a gas inlet port 742 that extends outwardly therefrom and is constructed to attach to a gas source. More specifically, the gas inlet port 742 is in fluid communication with and provides an entrance into the first connector 740 and is in the form of a tubular structure that has a distal end 744. The end 744 is meant to be attached to the gas source by any number of techniques, including using a gas conduit, such as tubing or the like, that extends from the gas source to the gas inlet port 742. The gas source is preferably connected to a control system or regulator or the like that permits the flow rate of the gas source to be carefully controlled and varied by means, such as valve assemblies and the like that are associated therewith (e.g., valve assembly within the gas conduit).

The gas source can hold any number of different types of gases that are intended for inhalation by the patient through the accessory 500.

In addition, the first leg 530 can contain a supplemental gas inlet port or connector 751 that extends outwardly therefrom and can be fluidly attached to a supplemental gas source. The gas inlet port 751 is formed so that it is above the first connector 740 when the first connector 740 is inserted into the first leg 530 so that the gas inlet port 751 does not interfere with the reception of the first connector 740 into the first leg 530.

The second connector 750 is similar to the first connector 740 and is in the form of a tubular connector that is both sized and shaped to fit intimately within the second leg 540. For example, the second connector 750 can be frictionally fit into and held within the second leg 540 as by slidingly engaging the second connector 750 within the second leg 540. The lengths of the first and second connectors 740, 750 are preferably the same.

The accessory 500 includes a number of different valve assemblies that are positioned within the body 510. More specifically, a first valve assembly 800 is disposed within the open first end 512 of the main section 520 and in the illustrated embodiment, the first valve assembly 800 functions as an exhalation valve. The first valve assembly 800 includes a valve element 802 which is positionable between an open position and a closed position and which can be any number of different types of valve structures so long as they function in the intended manner and provide the desired results. The valve 802 typically seats against a valve seat that is formed at the first end 512 when the valve 802 is closed. The illustrated valve 802 is a one-way flap valve that presses against the valve seat on inhalation and completely occludes the open first end 512 to prevent any room air entrainment (i.e., not allowing the air from the atmosphere to enter into the main section 520 on inhalation). On exhalation, the flap valve 802 moves away from the flap valve seat for the air exhaled by the patient to escape into the atmosphere from the main section 520 by flowing through the fourth leg 560 from a mask or the like and then through the main section 520 and through the opening formed at the first end 512. The open first end 512 is the only means for the exhaled air to escape as will be appreciated below.

A second valve assembly 810 is provided and functions as a first inhalation valve in that the valve moves between an open position and a closed position depending upon whether the patient is inhaling or exhaling. The second valve assembly 810 is disposed within the first leg 530 when the holding chamber is attached thereto and in particular, the second valve assembly 810 includes a valve element 812 that is disposed at the free distal end of the connector 740.

The second valve assembly 810 includes a valve element 812 that can be any number of different types of valve structures so long as they function in the intended manner and provide the desired results. The valve 812 typically seats against a valve seat that is formed at the distal end of the connector 740. The illustrated valve 812 is a one-way flap valve that presses against the valve seat on exhalation and completely occludes the first leg 530 to prevent any exhaled air to flow from the mask through the main section 520 and into the first compartment 710. The valve element 612 is thus positioned so that the gas inlet port 742 is disposed between the valve element 812 and the first compartment 710. Thus, the closing of the valve element 812 prevents exhaled gas from flowing into the gas inlet port 742.

It will be appreciated that instead of incorporating the valve element 812 into the connector 740, the valve element 812 can be directly incorporated into the first leg 530 such that it still selectively permits fluid flow from the first compartment 710 and from the gas inlet port 742.

The valve element 812 is thus positioned so that the gas inlet port 742 is disposed between the valve element 812 and the first compartment 710. Thus, the closing of the valve element 812 prevents exhaled gas from flowing into the gas inlet port 742.

A third valve assembly 820 is provided and functions as a second inhalation valve in that the valve moves between an open position and a closed position depending upon whether the patient is inhaling or exhaling. The third valve assembly 820 is disposed within the main section 520 and in particular, the third valve assembly 820 is disposed within the main section 520 between the first and second legs 530, 540. In addition, the third valve assembly 820 is disposed between the fourth leg 560 and the second leg 540.

The third valve assembly 820 includes a valve element 822 that can be any number of different types of valve structures so long as they function in the intended manner and provide the desired results. The valve 822 typically seats against a valve seat 824 that is formed within the main section 520. The illustrated valve 822 is a one-way flap valve that presses against the valve seat 824 on exhalation and completely occludes the main section 530 to prevent any exhaled air to flow from the mask through the main section 520 and into the first compartment 710.

Both the first and second inhalation valves 812, 822 close when the patient exhales and conversely open when the patient inhales. Thus, when the patient exhales and the valves 812, 822 close, the exhaled gas travels down the fourth leg 560 into the main section 520; however, none of the first, second and third legs 530, 540, 550 are accessible and therefore, the exhaled gas must flow to the exhalation valve 802, which is open and thus, the exhaled gas flows out of the main section 820.

While the two compartments 720, 730 of the bag 710 are illustrated as having equal or about equal volumes, it will be appreciated that the bag 710 can be constructed so that one of the compartments 720, 730 has a greater volume. For example, the first compartment 720 that serves as the nebulizer holding compartment can have a greater volume than the second compartment 730 which receives the supplemental gas to backup the nebulized medication holding chamber.

In this embodiment, there is a single main gas source as opposed to the two gas sources of the previous embodiments. A single main gas source 900 is provided and a first conduit section 910 is connected at a first end 912 to the gas source 900, while an opposite second end 914 is connected to a conduit adapter or connector 920. The connector 920 is a Y connector in that it has a first leg 922 that is connected to the second end 914 of the conduit 910, as well as second and third legs 924, 926, respectively. Fluid flow (gas from source 900) is thus delivered into the first leg 922 and then split into two flow paths, namely, those defined by the second and third legs 924, 926. A second conduit section 930 is connected at a first end 932 to the second leg 924 and a separate third conduit section 940 is connected at a first end 942 to the third leg 926. An opposite second end 934 of the second conduit section 930 is connected to the gas inlet port 742 to deliver gas from the source 900 into the first compartment 710 and/or into the main section 520 by traveling through the first leg 530. An opposite second end 944 of the third conduit section 940 is connected to either the nipple 705 that is part of the cap 701 or the conduit 620 of the nebulizer body 610 depending upon whether the nebulizer 600 is installed in the third leg 550 or whether the cap 701 is installed in the third leg 550. In either instance, gas flows through the second conduit section 930 and into the third leg 530. When it is desired to deliver aerosolized medication to the patient, then the nebulizer 600 is installed in the third leg 550 and the second conduit section 930 is connected to the conduit 620 to permit gas to flow from main gas source 900 to the nebulizer 600 where the medication is aerosolized.

The use of a single main gas source 900 compared to two separate gas sources (as in the other embodiments) provides a number of advantages. First, the use of a single source is more economical and simpler in design since only one supply of gas is needed. Consequently, less space is consumed since only one gas tank is needed. In addition, since only one gas is used, the flow rates and the formulations for the patient can be more easily controlled and monitored.

When operating the accessory 500 with the nebulizer 600, the nebulizer 600 is inserted into the third leg 550. The second leg 540 remains capped for most applications and the gas input (conduit 620) of the nebulizer 600 becomes the third port of the accessory 600. The second and third legs 540, 550 are constructed as gas inlet ports that utilize gas tubing.

In accordance with one aspect of the present invention, the dimensions of the gas inlet port 742 and the conduit 620 of the nebulizer 600 are carefully selected to optimize the performance of the nebulizer 600. In particular, the gas inlet port 742 is constructed so that it has dimensions (e.g., diameter) less than the dimensions of the conduit 620 of the nebulizer 600. For example, the spray hole for commercially available nebulizers 600 ranges from about 0.022 inches to about 0.025 inches. The resultant flows in the tubing (port 742 and conduit 620) are as follows when using 15 LPM (liters per minute) Ox (the maximal measurable flow for commercially available flow meters for air and oxygen). For example, the diameter for port 742 is identified as P1 and can have a diameter of between about 0.020 inches and 0.025 inches and the diameter for conduit 620 (nebulizer spray hole) is identified as P3 and can have a diameter of between about 0.022 inches and 0.025 inches. However, in the various exemplary embodiments, the size of the port 742 is less than the size of the conduit 620 (nebulizer spray hole). The ratio for the two openings determines the ratio of the two gas flows through the port 742 and conduit 620.

If P1>P3, then more than half of the flow will go through the gas tubing to the gas inlet port 742. The nebulizer 600 will receive less than 7.5 LPM of flow. If P1 is substantially greater than P3, then the flow to the nebulizer 600 will be much less than 7.5 LPM. Since most single treatment nebulizers require 8 LPM to 12 LPM to work optimally, this condition is less than ideal. If P1=P3, then half of the flow will go through the tubing to the port 742. The nebulizer 600 will receive 7.5 LPM of flow. Since most single treatment nebulizers require 8 LPM to 12 LPM to work optimally, this condition is less than ideal although, the nebulizer 600 will be useable.

If P1<P3, then more than half of the flow will go through the tubing to port (conduit) 620. This nebulizer receive more than 7.5 LPM of flow. Since most single treatment nebulizers 600 require 8 LPM to 12 LPM to work optimally, this condition is ideal as long as P1>P3 but not when P1 is substantially greater than P3 since the flow to the nebulizer will approach 15 LPM and the tubing disconnect from port 620 due to back pressure. For the case, where P1>P3 within about 20%, we observe that the nebulizer 600 will see approximately 20% more than half the flow. Thus, the nebulizer 600 would receive a flow of about 9 LPM which is within most nebulizer optimal operating parameters.

Thus, for the given total flow to the system, the ratios of the flows through P1 and P3 are dependent on the ratios of the ($r^4$) of the two holes, where r is the radius of the opening. Thus, the flow through port 742/the flow through port 620 is equal or approximately equal to [(radius port 742)$^4$]/[(radius port 620)$^4$]. The spray hole (conduit 620) for commercially available nebulizers range from about 0.022 inches to about 0.025 inches. So, if port 742 has a radius of about 0.020 inches, this allows for flow ranging from 8.5 LPM to about 11 LPM. It will also be appreciated that the above optimization techniques for the sizing of the ports 742, 620 is not limited to the situation where the gas is air, but instead, other gases, such as heliox which is very much less dense, can be used. If the port 742 had the same dimensions as the conduit 620, the greater part of the gas would flow through port 742 and consequently, the nebulizer 600 would not get sufficient gas flow. Since the gas is lighter than Ox, even less gas would go to the nebulizer 600. When heliox is used, the flow rate can be set at 16.5 LPM using a flow meter designed for use with heliox. Since heliox gas requires a higher flow rate than oxygen to nebulize the same dose output, higher flows have to be set up with the heliox flow meters. Otherwise, correction factors have to be used in order to determine the correct reading that corresponds to 16.5 LPM. Flows of 10 LPM to 14 LPM are recommended for nebulizer operation.

Flows through the second and third conduit sections 930, 940 to the ports 742, 620, respectively, determine the resultant flow to the nebulizer 600. This is in part due to ratios of the hole sizes stated above. Once the flow window for port 610 (the nebulizer 600) has been determined to be within about 8 LPM to about 12 LPM., optimal operation for nebulization is assured. Port 742 can be used to dilute a given gas used (such as oxygen or premixed heliox, through ports 742, 620). This is done by using the original gas with the Y tubing and then opening port 742 to outside air or by using a second gas source to deliver air at a fixed rate. Alternatively, another gas could be used through port 742 and in one embodiment, anesthesia gas can be introduced into the port 742.

It will be appreciated the control and metering of the respective gas flows can be accomplished in any number of different ways so long as the flow rate of the supplemental gas can be controlled so that there is a defined relationship between the flow rates of the primary gas delivered to the nebulizer and the supplemental gas. For example, the flow rate of the supplemental gas is less than the flow rate of the primary gas to the nebulizer and the flow rate of aerosolized medication to the main conduit body.

Figure 8:
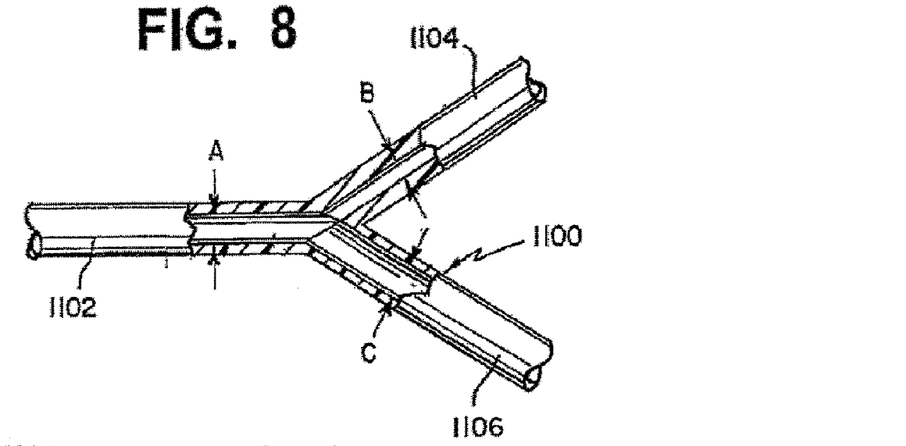
FIG. 8 is a cross-sectional view of a Y-tubing according to one embodiment and intended to provide metering of the delivered fluids.

For example and as shown in FIG. 8 and FIG. 6, the metering of the supplemental gas can occur not at a location remote from the gas inlet port 742 and location remote from the third leg 550 or the nipple 705 or other inlet port connected to the third leg 550. Instead, the metering occurs prior to delivery of the gases to the respective gas inlet port 742 and third leg 550. More specifically and according to one embodiment, the metering occurs by means of a connector or conduit 1100 that is attached to the various working components such that the metering of the gases occurs external to the accessory, such as accessory 500. In the embodiment of FIG. 8, the member 1100 is in the form of Y-tubing that attaches to the various components. The conduit/tubing 1100 includes a first leg (tube section) 1102, second leg (tube section) 1104, and third leg (tube section) 1006. The first leg 1102 connects to the gas source 900, the second leg 1104 connects at its distal end to gas inlet port 742, and the third leg 1106 connects at its distal end to the gas inlet of the nebulizer 600.

In accordance with one embodiment, the inner diameters of the various legs of the Y-tubing 1100 are constructed to perform the metering operation and control the flow rate of the respective gases. In particular, the second leg 1104 of the tubing 1100 has an inner diameter B that is less than the inner diameters A, C of the legs 1102, 1106, respectively, resulting in a decreased fluid flow rate through the second leg 1104 relative to the other legs 1102, 1106. The flow rate of the supplemental gas is at a reduced rate (less than) the flow rate of the primary gas that is delivered to the nebulizer 600 for generating the aerosolized medication. The inner diameter C of the leg 1106 that is connected to the nebulizer 600 is typically less than the inner diameter A of the first leg 1102 that is connected to the gas source 900 since it is desired to have the greatest flow rate entering the tubing 1100 before the gases are split into two flow paths for delivery to the gas inlet port 942 and nebulizer 600. By having two different inner diameters, the flow rates of the respective gases are controlled in the manner described above with respect to the other embodiments.

It will be appreciated that in FIG. 8, the outer diameters of all three legs 1102, 1104, 1106 of the tubing 1100 are the same so as to give the connector 1100 a uniform appearance and permit any one of the legs to be attached to a standard sized port that is part of equipment that is used in the inhalation system. In order for the inner diameters of the legs to be different, the wall thickness of the legs is different. In other words, the wall thickness of the leg 1104 is greater so as to create a smaller inner diameter B of the leg 1104 as discussed above without impacting its outer diameter.

It will also be appreciated that the tubing 1100 replaces the components 910, 920, 930, and 940. However, in another embodiment, the tubing 910, 930, 940 has the same construction (shape and size) and the above-described metering takes place in the Y-connector (e.g., 920 in FIG. 6) that connects to all the tubings. The varying inner diameters A, B, C described above with respect to the tube sections are incorporated into the legs 922, 924, 926 of the connector. In other words, the connector 924 (FIG. 6) has a smaller inner diameter than the other legs to meter the gas being delivered to the supplemental gas inlet port 742. In this embodiment, the metering still takes place external to the accessory 500 and not at the gas inlet port 742. In this embodiment, the conduits 930, 940 that carry the primary and supplemental gases, respectively, can have the same inner diameter or can have a different diameter relative to the inner diameters of the metering legs of the Y-connector. Additionally, the inner diameters of the conduits 930, 940 can be the same or can be different with respect to one another.

It will be appreciated that in this case, the supplemental and primary gases are from the same source, namely, gas source 900 (FIG. 6).

Figure 9:
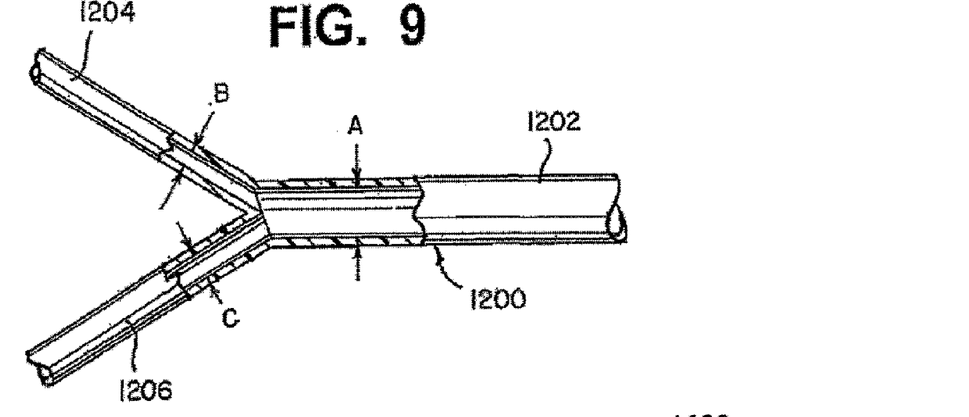
FIG. 9 is a cross-sectional view of a Y-tubing according to another embodiment and intended to provide metering of the delivered fluids.

FIG. 9 shows another embodiment that is similar to the embodiment of FIG. 8 and includes a Y-tubing 1200 having a first leg or tube section 1202, a second leg or tube section 1204, and a third leg or tube section 1206. In this embodiment, not only are the inner diameters of at least two legs 1202, 1204, 1206 different, but the outer diameters of at least two 1202, 1204, 1206 are also different. The leg 1204 that has the smallest inner diameter B, likewise has the smallest outer diameter and the leg 1202 that has a larger inner diameter A, likewise has a larger outer diameter. The inner diameter C of the leg 1206 is greater than inner diameter B and can be equal to or less than the inner diameter A. The outer diameter of the leg 1206 is greater than the outer diameter of the leg 1204 and can be equal to or less than the outer diameter of leg 1202.

As with the Y-tubing 1100, the tubing 1200 performs the metering function and this occurs outside or external to the accessory 500.

In another embodiment, the metering is performed in a Y-connector that attaches to tubing that attaches to the accessory (e.g., accessory 500). As described above, the legs of the Y-connector have different inner and outer diameters. In this embodiment, the tubing or conduits that are attached to the various legs are of different sizes and have different inner diameters in order to permit the tubing to mate with the different sized legs of the connector. The tubing that attaches to the leg for delivering the supplemental gas to the gas inlet port 742 has the smallest inner diameter compared to the other tubing. In this manner, by controlling the inner diameters of the legs of the connector and the conduits that attach thereto, the flow rates of the gas from source 900 can be controlled so as to result in an effective metering of the gas into the respective gas inlet port 742 and the third leg 550.

Figure 10:
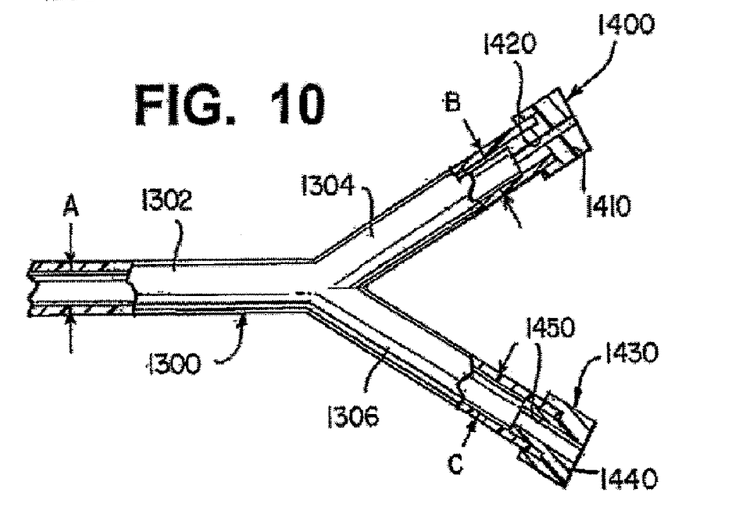
FIG. 10 is a cross-sectional view of a Y-tubing according to one embodiment and intended to provide metering of the delivered fluids.

Now referring to FIG. 10 in which a connector or Y-tubing 1300 according to another embodiment of the present invention is shown. The connector 1300 is similar to Y-tubing 1100 in that the outer diameters of the legs (tube sections) 1302, 1304, 1306 are the same. In this embodiment, one or more plugs 1400 or the like are inserted into the open ends of one or more legs of the Y-tubing 1100 in order to effectively reduce the size of the free opening of the leg. In other words, the leg itself of the Y-tubing 1300 contains the plug 1400 that effectively reduces the diameter of the opening of the leg, thereby reducing the rate at which the gas flows into the respective gas inlet port 742, nebulizer 600 or the like.

The plug 1400 includes a plug body 1410 that is inserted into the opening of the leg (tube section) and is held therein by a mechanical fit (frictional fit). The body 1410 includes a through bore or channel 1420 that passes there through and is in communication with the interior of the leg to permit fluid flowing through the leg to exit through the plug. The diameter of the channel 1420 performs the metering function and therefore, by varying the diameter of the channel 1420, the fluid is metered.

As shown in FIG. 10, the free end of the leg (tube section) 1304 that is connected to the gas inlet port 742 includes one plug 1400 having channel 1420 defined by a first diameter. By inserting the plug 1400 into the free end of the leg 1304, the flow of gas is restricted by means of the opening 1420 since the gas must flow through the opening 1420 in order to flow into the gas inlet port 742. It will be appreciated that the metering performed by the leg 1304 can be easily changed and varied by simply inserting a new plug that has a channel with a different diameter. For example, if a lower effective flow rate of the supplemental gas to the gas inlet port 742 is desired, then a plug with a smaller diameter channel is inserted in free, open end of the leg 1304.

Similarly, the free end of the leg 1306 that attaches to the nebulizer 600 can contain a second plug 1430 that has a body 1440 with an opening 1450 having a second diameter. The leg 1302 that is attached to the gas source 900 does not necessarily have a plug; however, it can have a plug if there is a need to reduce the flow of the gas from the gas source 900 into the other legs 1304, 1306.

The plugs can simply be a member that includes a stem that is inserted into the conduit or connector leg with one end of the plug having a disc-shaped body through which the respective opening is formed to permit passage of the fluid.

The member (tube leg) in which the plug is inserted can be coupled to the gas inlet port 742 or the nebulizer 600 by any number of different means including simply inserting the plug into either gas inlet port 742 or the nebulizer inlet port. For example, when the first plug 1400 is formed at one end of the leg 1304, the end including the plug 1400 is inserted into the gas inlet port 742 to establish a secure coupling (e.g., frictional fit) between the two. It will be appreciated that as gas flows through the leg 1304, the flow of gas is restricted due to the reduced diameter of the opening in the plug 1400. The use of a plug, which can be removed and replaced with another plug having an opening that has a different diameter, permits precise control of the flow rate of the gas into the accessory disclosed herein.

Thus, the metering aspect of the present invention is not limited to being incorporated as part of the accessory itself but instead, can be incorporated into either a connector, such as a Y-connector, that is used to split a gas flow path into multiple paths that are delivered to the supplemental gas inlet port and the primary gas inlet port that is in communication with the nebulizer, or it can be incorporated into the conduit (Y-tube) structure that is attached to the secondary gas inlet port and/or the gas inlet port into the nebulizer. In this manner, the first compartment 720 receives less of a gas flow than the second compartment 730 due to the gas flow into the nebulizer being greater than the gas flow rate into the gas inlet port 742 and ultimately into the first compartment 720.

In the embodiments of FIG. 8-10, the accessory can be constructed so that the inner diameter of the connector leg or the conduit that is coupled to the nebulizer 600 is at least 10% greater than the inner diameter of the connector leg or the conduit that is coupled to the supplemental gas inlet port 742. In another embodiment, the inner diameter of the connector leg or the conduit that is coupled to the nebulizer 600 is between about 10% to about 20% greater than the inner diameter of the connector leg or the conduit that is coupled to the supplemental gas inlet port 742. In accordance with one embodiment, the gas is oxygen and the two inner diameters are selected so that the nebulizer receives a flow rate between about 8 LPM (liters per minute) to about 12 LPM. In another embodiment, the gas is heliox and the two inner diameters are selected so that the nebulizer receives a flow rate of about 16.5 LPM.

It will be appreciated that the above dimensions are merely exemplary and the components can have dimensions that lie outside the above ranges so long as the desired results, as discussed above, are achieved.

With reference to the prior figures, it will also be appreciated that a flow metering structure can be in the form of a connector or tubing that is attached to the single source of gas and is constructed to divide the gas flow into two distinct flow paths with one flow path being delivered to a nebulizer where the aerosolized medication is generated and another flow path is delivered to an accessory to supply supplemental gas to the patient under select conditions (e.g., when the supply of aerosolized medication is inadequate). Each of the conduits that supply the supplemental gas and the gas to the nebulizer includes a flow restrictor member that serves to control the flow rate of the supplemental gas and the flow rate of the gas to the nebulizer. In one embodiment, the flow restrictor member can be placed anywhere along the conduit. For example, the flow restrictor can be disposed at the end of the conduit or it can be placed a predetermined distance from the end of the conduit. The flow restrictor can be a plug, such as the one described above, or one which can be inserted into the conduit and positioned at a location along its length. The flow restrictor has an orifice that restricts and controls the flow of the gas through the conduit. In other words, the flow restrictor can be a diaphragm like structure that is positioned within the conduit anywhere along its length.

In one embodiment, the conduit that delivers the supplemental gas to the accessory is in the form of a leg of a connector (e.g., Y connector) and the conduit that delivers the gas to the nebulizer is in the form of a different leg of a connector. In another embodiment, the conduit that delivers the supplemental gas to the accessory is in the form of a length of tubing (e.g., Y tubing) and the conduit that delivers the gas to the nebulizer is in the form of a length of tubing.

It will also be appreciated that the distance between the location where the conduits split into two different pathways and the location of the single gas source is variable. In other words, the location of the single gas source relative to the patient is variable. The gas from the single gas source can be divided into two flow paths at a location proximate the single gas source itself or the gas can be divided at a location that is closer to the interface and the patient. In this case, the location of the gas split is near the nebulizer as well.

In yet another embodiment, the flow control means in each of the first and second flow paths is in the form of a controllable valve device. For example, a first valve device can be disposed in the first conduit and a second valve device can be disposed in the second conduit. By controlling the respective flow rates in the first and second flow paths, the flow of the supplemental gas to the accessory and the flow of the primary gas to the nebulizer are controlled in the same manner described herein with respect to the other embodiments. The controllable valve devices are connected to a controller which operates the valves so as to control and set the flow rates in the conduits according to predetermined values. The controllable valve devices can be arranged so that there is a predetermined ratio between the flow rates and in particular, the ratio can be one of the ones discussed hereinbefore.

The above configurations serve to meter the supplemental gas and primary gas prior to delivery to the accessory and the nebulizer, respectively. This requires no modifications to be done to the accessory and nebulizer themselves.

Having described embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. An aerosol inhalation system comprising:
   a single source of gas;
   a Y-conduit having a first leg in fluid communication with the gas source and second and third legs, wherein the second leg has a first inner diameter and the third leg has a second inner diameter that is less than the first diameter;
   an accessory having a main conduit body and a patient interface conduit that is adapted to deliver aerosolized medication to a mouth of the patient;
   a nebulizer sealingly and removably coupled to the main conduit body, the nebulizer including a gas inlet port that is fluidly connected to the third leg of the Y-conduit to permit gas from the single source to flow into the nebulizer to create the aerosolized medication that is delivered into the main conduit body and to the patient through the patient interface conduit; and
   a supplemental gas inlet port that is part of the main conduit body and is fluidly connected to the second leg of the Y-conduit for introducing a flow of supplemental gas from the single gas source to the patient interface under select conditions;
   a holding chamber having a first compartment and a second compartment separated from the first compartment, with the first compartment being sealingly and fluidly coupled to a first port of the main conduit body and the second compartment being sealingly and fluidly coupled to a second port of the main conduit body, wherein the holding chamber is defined by a reservoir bag with the first and second compartments defined therein and separated from one another by a bi-furcating wall, the reservoir bag being formed of an expandable/collapsible material; and
   an arrangement of valves such that when the patient exhales, the first and second compartments are sealingly closed off from the patient interface conduit resulting in exhaled air being delivered to a first end of the main conduit body that is selectively open when the patient exhales and conversely, when the patient inhales, the first and second compartments are opened to the main conduit body resulting in the aerosolized medication being delivered through the main conduit body to the patient interface conduit and to the patient; and
   wherein the second leg has a flow metering structure associated therewith for controlling the flow rate of the supplemental gas to the patient interface, the flow rate of the gas through the supplemental gas inlet port being different than a gas flow rate through the third leg into the nebulizer for generating the aerosolized medication, whereby the reduced inner diameter of the second leg acts as the flow metering structure since the flow rate of supplemental gas is controlled and reduced by flowing through the second leg relative to the flow rate of gas through the third leg.

2. The accessory of claim 1, wherein the outer diameters of the second and third legs have the same outer diameters.

3. The accessory of claim 1, wherein the outer diameter of the second leg is less than an outer diameter of the third leg.

4. The accessory of claim 1, wherein the inner diameter of the third leg is at least 10% greater than the inner diameter of the second leg.

5. The accessory of claim 1, wherein the arrangement of valves includes an exhalation valve that moves between an open position when the patient exhales, thereby opening the main conduit body to atmosphere and a closed position when the patient inhales.

6. An aerosol inhalation system comprising:
   a single source of gas;
   a Y-conduit having a first leg in fluid communication with the gas source and second and third legs;
   an accessory having a main conduit body and a patient interface conduit that delivers aerosolized medication to a mouth of the patient;
   a nebulizer sealingly and removably coupled to the main conduit body, the nebulizer including a gas inlet port that is fluidly connected to the third leg of the Y-conduit to permit gas from the single source to flow into the nebulizer to create the aerosolized medication that is delivered into the main conduit body and to the patient through the patient interface conduit; and
   a supplemental gas inlet port that is part of the main conduit body and is fluidly connected to the second leg of the Y-conduit for introducing a flow of supplemental gas from the single gas source to the patient interface under select conditions; and
   a holding chamber having a first compartment and a second compartment separated from the first compartment, with the first compartment being sealingly and fluidly coupled to a first port of the main conduit body and the second compartment being sealingly and fluidly coupled to a second port of the main conduit body, wherein the holding chamber is defined by a reservoir bag with the first and second compartments defined therein and separated from one another by a bi-furcating wall, the reservoir bag being formed of an expandable/collapsible material;
   wherein the second leg has a flow metering structure associated therewith for controlling the flow rate of the supplemental gas to the patient interface, the flow rate of the gas through the supplemental gas inlet port being different than a gas flow rate through the third leg into the nebulizer for generating the aerosolized medication.

7. A method for providing an aerosolized medication to a patient comprising the steps of:
provide a single gas source;
providing a connector that is configured to divide gas flow from the single gas source into a first flow path that is fluidly connected to a supplemental gas port of an accessory that is part of an aerosol inhalation device and a second flow path that is fluidly connected to a nebulizer, the gas in the first flow path being supplemental gas and the gas in the second flow path being primary gas;
controlling a flow rate of the supplemental gas in the first flow path by constructing the connector so that the first flow path therein has a first width;
controlling a flow rate of the primary gas in the second flow path by constructing the connector so that the second flow path therein has a second width that is different than the first width and therefore is more restrictive as to gas flow;
delivering the aerosolized medication from the nebulizer to the accessory where it is delivered to the patient when the patient when the patient inhales;
storing the supplemental, nonmedicated gas in a first reservoir that has a fixed volume and is part of the accessory and delivering the supplemental, nonmedicated gas to the patient when the flow of the aerosolized medication is below a threshold value; and
storing the aerosolized medication in a second reservoir that has a fixed volume and is part of the accessory, the second reservoir being fluidly connected at all times to a main port through which the aerosolized medication flows to permit the aerosolized medication to flow therein and be stored when the patient exhales or when there is excess amount of aerosolized medication;

wherein the flow rate of the supplemental gas is different than the flow rate of the primary gas as a result on the construction of the connector.

8. The method of claim 7, wherein the step of delivering the supplemental, no medicated gas to the patient comprises the step of opening an inhalation valve that is positioned between the supplemental gas port and a main body of the accessory which includes an interface for the patient, the first reservoir separated from the main body section by the inhalation valve and accordingly, supplemental gas stored in the first reservoir is delivered to the main body section and the patient only when the inhalation valve opens.

9. The method of claim 7, wherein the flow of the supplemental gas is metered at a location that is remote from the accessory and the flow of the primary gas is metered at a location that is remote from the nebulizer.

10. The method of claim 7, wherein the first flow path is defined by a first leg of the connector and the second flow path is defined by a second leg thereof and the method includes the following steps:

controlling the flow rate of the supplemental gas by incorporating a first flow restrictor element into the first leg; and controlling the flow rate of the primary gas by incorporating a second flow restrictor into the second leg.

11. The method of claim 10, wherein the first flow restrictor comprises a member that is placed anywhere along a length of the first leg, the first flow restrictor having an orifice that defines and controls the first flow rate and wherein the second flow restrictor comprises a member that is placed anywhere along a length of the second leg, the second flow restrictor having an orifice that defines and controls the second flow rate.

12. The method of claim 10, wherein the first flow restrictor comprises a first controllable valve that is disposed along the first flow path and the second flow restrictor comprises a second controllable valve.

13. The method of claim 7, wherein the first and second reservoirs are defined by a reservoir bag with the first and second reservoirs being in the form of first and second compartments defined therein and separated from one another by a bi-furcating wall, the reservoir bag being formed of an expandable/collapsible material.

* * * * *